United States Patent [19]
Mitchell et al.

[11] Patent Number: 4,875,492
[45] Date of Patent: Oct. 24, 1989

[54] WASHABLE AND CONTOURED NURSING PADS

[76] Inventors: Debra J. Mitchell, 1052 Windjammer Cir., Foster City, Calif. 94404; Cheryl L. Ranzau, 1073 Laurie Ave., San Jose, Calif. 95125

[21] Appl. No.: 190,666

[22] Filed: May 5, 1988

[51] Int. Cl.⁴ .............................................. A61F 13/14
[52] U.S. Cl. .................................. 128/890; 604/366; 604/370; 604/377; 604/378; 604/381; 604/383
[58] Field of Search ................... 128/889, 890, 112.1, 128/113.1, 114.1, 117.1, 156; 604/370, 375, 380, 371, 377, 378, 381, 383, 365–367; 450/37

[56] References Cited

U.S. PATENT DOCUMENTS

| | | | |
|---|---|---|---|
| 2,492,303 | 12/1949 | Cascio | 128/890 X |
| 2,864,362 | 12/1958 | Hermanson et al. | 604/366 X |
| 2,891,544 | 6/1959 | London | 450/37 X |
| 3,262,451 | 7/1966 | Morse | 604/370 |
| 3,356,090 | 12/1967 | Plantinga et al. | 450/37 X |
| 3,442,268 | 5/1969 | Bird | 604/370 X |
| 3,738,362 | 6/1973 | Sneider | 604/370 X |
| 4,047,534 | 9/1977 | Thomaschefsky | 128/461 |
| 4,074,721 | 2/1978 | Smits | 128/461 |
| 4,125,114 | 11/1978 | Repke | 604/366 |
| 4,164,228 | 8/1979 | Weber-Unger | 128/150 |
| 4,193,404 | 3/1980 | Repke et al. | 604/366 |
| 4,275,105 | 6/1981 | Boyd et al. | 604/370 X |

*Primary Examiner*—Robert A. Hafer
*Assistant Examiner*—Kevin G. Rooney
*Attorney, Agent, or Firm*—Debra J. Mitchell; Cheryl L. Ranzau

[57] ABSTRACT

A washable and contoured nursing pad which can be machine washed and dried, and therefore resuable and economical. The nursing pad is molded into a contoured shape for a body-hugging fit inside the wearer's bra. The nursing pad consists of multiple layers of different types of fabrics for different functions, including a decorative and slip resistant lace outer layer, a waterproof second layer, a fluid absorbent third layer, and a soft comfortable inner layer.

1 Claim, 1 Drawing Sheet

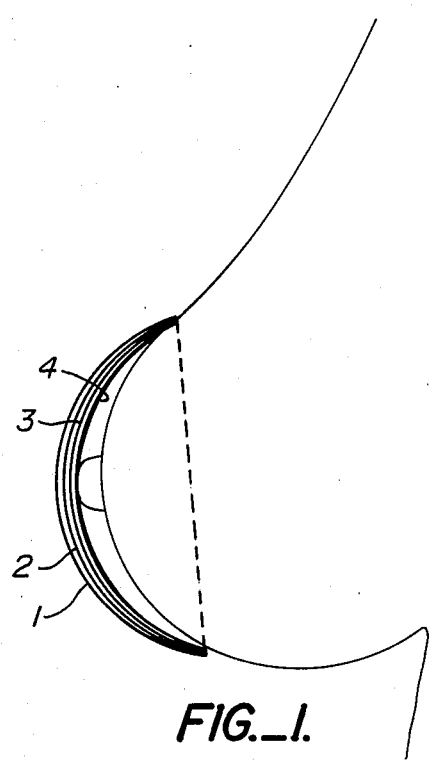
FIG._1.
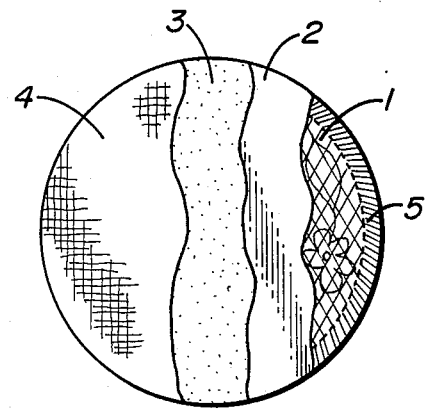
FIG._3.
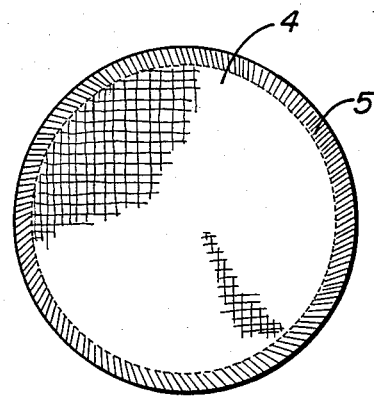
FIG._2.

WASHABLE AND CONTOURED NURSING PADS

BACKGROUND OF THE INVENTION

1. Field of the Invention

The present invention relates to the field of nursing pads. More particularly, the present invention relates to a washable and therefore reusable nursing pad which is molded into a contoured shape for a body-hugging fit inside the wearer's bra consisting of multiple layers of different types of fabrics for different functions.

2. Description of the Prior Art

Although there are multiple layer disposable nursing pads on the market, they cannot be washed and reused since the fibers used in their construction cannot withstand the stress of machine washing or the high temperatures of machine drying necessary to kill bacteria present on the nursing pad. Examples of these disposable nursing pads are described in the U.S. Pat. No. 4,047,534, 4,074,721 and 4,164,228.

Disposable nursing pads have additional disadvantages in that they are expensive in comparison to washable nursing pads. Although the unit price per nursing pad is greater for washable nursing pads, they can be machine washed and dried and reused numerous times making them more economical over the long term when compared with disposable nursing pads.

Disposable nursing pads are made of fibers which often cause skin irritation. A higher incidence of skin irritation is associated with disposable nursing pads which can lead to breast infection.

The fabrics of the washable nursing pad of the present invention have been selected to minimize those problems which are prevalent among disposable nursing pads.

U.S. Pat. No. 4,047,534 issued to Thomaschefsky in 1977, U.S. Pat. No. 4,074,721 issued to Smits in 1978, and U.S. Pat. No. 4,164,228 issued to Weber-Unger in 1979, describe nursing pads which are disposable.

Thomaschefsky U.S. Pat. No. 4,047,534 issued in 1977, describes a disposable nursing pad which is not washable, and therefore is not reusable or economical. It's multi-ply construction of thermoplastic polymeric microfibers are thin enough to be conformable and highly absorbent. These thermoplastic polymeric microfibers further provide non-slippage inside the wearer's bra. However, said fibers can increase the chance of skiin irritation which can lead to breast infection.

U.S. Pat. No. 4,074,721 issued to Smits in 1978 describes a disposable nursing pad which is contoured and comprised of a plurality of layers of fiber wherein the central layer has a high degree of absorbency. However, it is not washable, and therefore is not reusable or economical. Additionally, the use of cellulose fiber comprised of bleached and macerated wood pulp increases the chance of skin irritation which can lead to breast infection. Another disadvantage of this prior art is that the pad has no slip resistant properties which can lead to displacement of the pad inside the wearer's bra.

Weber-Unger U.S. Pat. No. 4,164,228 issued in 1979 describes a disposable nursing pad which is contoured with an absorbing apron attached to the can-shaped part, andn said apron increases the absorption volume of the pad as a whole. One disadvantage in this prior art is that the apron, which hangs down below the wearer's bra, could cause fluid to wick onto the wearer's clothing. A further disadvantage is that it is not washable, and therefore is not reusable or economical. Still another disadvantage of this prior art is that the pad has no slip resistant properties which can lead to displacement of the pad inside the wearer's bra.

SUMMARY OF THE INVENTION

The present invention is a washable, and therefore a reusable and economical nursing pad which is molded into a contoured shape for a body-hugging fit inside the wearer's bra consisting of multiple layers of different types of fabrics for different functions.

The nursing pad has a contoured shape for a body-hugging fit due to its unique molded construction, which does not wash out. After molding, the fabrics do not have "memory" of their original flat shape, and therefore retain their contoured shape even after numerous washings. This contoured shape is designed so that one size fits all. Even if the outside edge of the nursing pad reaches beyond the breast to the wearer's chest, it will fit a small bra cup wearer. Should the wearer be well-endowed, the pad will still cover and collect fluid.

The different functions performed by the multiple layers of fabrics include a decorative and slip resistant lace outer layer, a waterproof second layer, a fluid absorbent third layer, and a soft comfortable inner layer. All four layers are comprised of fabrics consisting of a significant amount of polyester (or other suitable moldable fabrics) in order that they be compatible in the fabric molding process.

The present invention further includes an overlock stitching of thread along the outer edge of the nursing pad to hold the layers of fabric together.

OBJECTS OF THE INVENTION

One object of the present invention is to provide a washable nursing pad which can be washed and dried numerous times by machine, thereby reducing the cost of nursing pad usage.

It is another object of the present invention to provide a washable nursing pad which is molded into a contoured shape for a body-hugging fit inside the wearer's bra which has a smooth and seamless appearance.

It is a further object of the present invention to provide a nursing pad which has a decorative lace outer layer whichc is slip resistant inside the wearer's bra.

It is yet another object of the present invention to provide a nursing pad with a waterproof second layer preventing the excreted fluid from passing through to the wearer's clothing.

It is yet a further object of the present invention to provide a nursing pad with a fluid absorbent third layer which absorbs excreted fluid.

It is still another object of the present invention to provide a nursing pad which is safe and non-irritating to the wearer's skin. The soft flannel inner layer has been selected to give a comfortable "stay-dry" feeling while wicking the fluid away from the wearer's body and into the fluid absorbent third layer, and yet retain the fluid inside the nursing pad, allowing the wearer to remain substantially dry.

It is still a further object of the present invention to include an overlook stitching of thread along the outer edge of the nursing pad to hold the layers of fabric together.

Other objects of the present invention will become apparent as the invention becomes more fully understood with reference to the accompanying drawings.

BRIEF DESCRIPTION OF THE DRAWINGS

FIG. 1 is a side elevation of the washable nursing pad of the present invention with a cutaway section showing the different layers of fabric.

FIG. 2 is a back plan view of the nursing pad of the present invention showing the inner side and the overlock stitching of thread thereof.

FIG. 3 is a top plan view of the nursing pad of the present invention with a partial cutaway section showing the different layers of fabric and the overlock stitching of thread.

DESCRIPTION OF THE PREFERRED EMBODIMENT

The preferred embodiment of the washable nursing pad of the present invention has a body-hugging configuration due to its unique form of construction via the molding process.

Referring to FIG. 1, the nursing pad is a one size fits all molded pad to provide a smooth and seamless fit. The fabrics used in construction of the nursing pad allow it is to reused through numerous machine washings and dryings.

The nursing pad is comprised of multiple layers of different types of fabrics for different purposes. The washable nursing pad in FIG. 1—1 includes an outer decorative lace and slip resistant layer, a waterproof second layer in FIG. 1-2, a fluid absorbent third layer in FIG. 1-3, and a soft and comfortable inner layer against the skin which wicks fluid away from the wearer's body and into the fluid absorbent third layer, and yet retains the fluid inside the nursing pad, allowing the wearer to remain substantially dry in FIG. 1-4.

The decorative outer layer of lace fabric provides an aesthetrically pleasing appearance. The preferred outer fabric is polyester lace which is slip resistant inside the wearer's bra.

The waterproof second layer forms a barrier to moisture penetration, preventing the excreted fluid from passing through to the outside of the nursing pad and onto the wearer's clothing. The preferred waterproof fabric is polyester tricot coated with polyvinylchloride. Coated polyester tricot or other such fabric is impermeable to moisture. Polyvinylchloride is used to waterproof a variety of fabrics, more specifically, fabrics used in the manufacturing of baby bibs, crib sheets, diapers, hospital sheeting and incontinent items. Polyvinylchloride lends itself to washing and drying temperatures up to 160 degrees Fahrenheit.

The fluid absorbent third layer is positioned adjacent to the waterproof layer and the lace layer. The fluid absorbent layer is made of a fluid absorbent fabric, such as felt, which is a needle punched fabric comprised of a rayon and polyester blend. The absorbent third layer may comprise one ply of fabric or may include a plurality of plies of absorbent fabric to increase the fluid absorbency of the nursing pad.

The nursing pad is further comprised of a soft and comfortable inner layer of brushed polyester flannel which is worn against the skin. The flannel wicks the fluid through to the absorbent needle punched felt and gives the feeling of a "stay-dry" layer.

A preferred embodiment of the nursing pad includes an overlock stitching of thread along the outer edge of the nursing pad to hold the layers of fabric together.

The present invention is more expensive per unit than disposable nursing pads presently on the market, but it can be washed and reused up to as many as 120 times. The benefits of the comfort ad safety of having a skin sensitive nursing pad which always retains its tensile strength so it cannot fall or be picked apart when it becomes wet are self-evident. These advantages are not obtainable from disposable nursing pads.

Thus, it will be seen from this description of the preferred embodiment of the present invention that the washable and contoured nursing pad disclosed and descibed herein achieves the objects and advantages attributable thereto, and while the invention has been described in considerable detail, it is not to be limited to such details as set forth except as may be necessitated by the appended claims.

I claim:

1. A washable and contoured nursing pad comprising a lace outer layer of a polyester lace with a rough side of the lace facing outward to prevent slipping inside the wearer's bra, a waterproof second layer which is comprised of a polyester tricot that is coated with 2.5 to 4 millimeters of opaque polyvinylchloride, a fluid absorbent third layer which is comprised of an 8 to 10 ounce needle punched felt blend of rayon and polyester, and a soft, and a comfortable inner layer adapted to be against the skin which is comprised of brushed polyester flannel and has a wicking quality which draws fluid through to the needle punched absorbent layer.

* * * * *